(12) United States Patent
Borrelli

(10) Patent No.: US 6,794,376 B2
(45) Date of Patent: Sep. 21, 2004

(54) METHODS AND COMPOSITIONS FOR ENHANCING DIFFUSION OF THERAPEUTIC AGENTS THROUGH TISSUE

(75) Inventor: Michael J. Borrelli, Troy, MI (US)

(73) Assignee: William Beaumont Hospital, Royal Oak, MI (US)

( * ) Notice: Subject to any disclaimer, the term of this patent is extended or adjusted under 35 U.S.C. 154(b) by 194 days.

(21) Appl. No.: 09/951,085

(22) Filed: Sep. 12, 2001

(65) Prior Publication Data

US 2002/0068717 A1 Jun. 6, 2002

Related U.S. Application Data

(60) Provisional application No. 60/251,713, filed on Dec. 6, 2000.

(51) Int. Cl.[7] ............................................... A61K 31/33
(52) U.S. Cl. ............................ 514/183; 515/1; 515/44; 515/431; 515/450
(58) Field of Search ............................. 514/1, 44, 183, 514/431, 450

(56) References Cited

U.S. PATENT DOCUMENTS

| | | | |
|---|---|---|---|
| 5,023,252 A | 6/1991 | Hseih | 514/183 |
| 5,620,479 A | 4/1997 | Diederich | 607/97 |
| 5,861,021 A | 1/1999 | Thome et al. | 607/101 |
| 5,922,013 A | 7/1999 | Fallik | 607/101 |
| 6,027,721 A | 2/2000 | Hammang et al. | 424/93.2 |
| 6,066,624 A | 5/2000 | Woo et al. | 514/44 |
| 6,093,392 A | 7/2000 | High et al. | 424/93.2 |
| 6,093,567 A | 7/2000 | Gregory et al. | 435/320.1 |
| 6,106,826 A | 8/2000 | Brandt et al. | 424/93.2 |
| 6,140,087 A | 10/2000 | Graham et al. | 435/91.42 |
| 6,140,111 A | 10/2000 | Riviere et al. | 435/320.1 |
| 6,167,313 A | 12/2000 | Gray et al. | 607/103 |
| 6,176,857 B1 | 1/2001 | Ashley | 606/32 |
| 6,245,347 B1 * | 6/2001 | Zhang et al. | 424/449 |

FOREIGN PATENT DOCUMENTS

WO     WO 98/29134     * 7/1998

OTHER PUBLICATIONS

Ghosh, et al., "Methods of enhancement of transdermal drug delivery: part IIB, chemical permeation enhancers," Pharmaceutical Technology 17 (5): 68–79, 1993.*

* cited by examiner

*Primary Examiner*—Scott D. Priebe
(74) *Attorney, Agent, or Firm*—Brinks Hofer Gilson & Lione

(57) ABSTRACT

The present invention provides methods and compositions for enhancing the diffusion of therapeutic agents through mammalian tissue. In one embodiment, invention provides methods and compositions useful for enhancing the diffusion of gene therapy vectors through a mammalian tissue of interest. The method comprises delivering the therapeutic agent and a permeabilizer to the tissue of interest. The method may further comprise inducing hyperthermia in the tissue. In one embodiment, a composition in accordance with the present invention comprises a gene therapy vector containing a polynucleotide and a tissue permeabilizer. A method of destroying tissue is also provided. In one embodiment of this aspect of the invention, the method includes delivering a high concentration of tissue permeabilizer to the tissue and may also include inducing hyperthermia in the tissue.

22 Claims, No Drawings

METHODS AND COMPOSITIONS FOR ENHANCING DIFFUSION OF THERAPEUTIC AGENTS THROUGH TISSUE

REFERENCE TO PREVIOUS APPLICATION

This application claims the benefit of U.S. Provisional Application No. 60/251,713 filed on Dec. 6, 2000.

FEDERALLY SPONSORED RESEARCH OR DEVELOPMENT

The United States Government may have rights in the present invention pursuant to the terms of grant number DAMD17-98-1-8496 awarded by the Army Prostate Cancer Initiative.

FIELD OF THE INVENTION

The present invention relates to methods and compositions for enhancing diffusion of therapeutic agents, such as gene therapy vectors, through tissue. Also, the present invention relates to methods and compositions for selectively destroying tissue.

BACKGROUND OF THE INVENTION

There are numerous applications in which a therapeutic agent is delivered to a tissue of interest. For example, gene therapy, in which the therapeutic agent comprises a vector carrying a polynucleotide, involves the introduction of DNA or RNA into one or more mammalian cells and/or tissues. Gene therapy holds great promise as a clinical treatment for a variety of human maladies, including various cancers, and many different therapeutic strategies have been devised. Examples of such strategies include replacement of an aberrant gene that caused cells to become malignant and inducement of tumor cells to manufacture a toxic substance that ultimately kills them.

A vector of some type is typically used to deliver the polynucleotide to the cells or tissue being treated. Viral vectors are currently the most frequently used vector in gene therapy procedures. Many different types of viruses can be used as the vector, with adenovirus and retrovirus being among the most commonly used.

In order for gene therapy to be successful, the vector must be delivered to the target tissue and successfully introduce the polynucleotide into the cells. Lastly, the genetic material carried by the vector must be ultimately located in the nucleus or other compartment of the host cell such that the polynucleotide, commonly referred to as a transgene or transgenes, can be expressed.

Frequently, delivery of the vector to the tissue of interest presents a significant challenge. The use of common systemic delivery methods, such as intravenous injection, is unattractive because it is typically desired to limit introduction of the transgene to a specific tissue. Furthermore, the transgene may produce a toxic substance. Thus, it is advantageous to limit exposure to the transgene to the tissue of interest. A simple approach to achieving this limited exposure has been to inject the viral vectors directly into the tissue of interest, usually a tumor or other diseased tissue. While this direct delivery does limit exposure of other tissues to the transgene, it also limits distribution of the transgene within the targeted tissue. Following injection, the majority of the injected vector load remains in the cells near the path created by the injection device. As a result, the volume of tissue that can be infected, and therefore treated, is restricted by the limited distance that the vector can diffuse through the intercellular space of the tissue.

SUMMARY OF THE INVENTION

The present invention provides methods of enhancing the diffusion of a therapeutic agent through tissue. A method in accordance with the present invention comprises delivering a permeabilizer to the tissue of interest. The permeabilizer is one or more member of a family of macrocyclic compounds previously used to enhance the rate at which a drug crosses skin membranes of various body cavities, the blood-brain barrier, and similar macroscopic membranes. This family of compounds is described in detail in U.S. Pat. No. 5,023,252 to Hsieh for TRANSDERMAL AND TRANS-MEMBRANE DELIVERY OF DRUGS, which is hereby incorporated by reference in its entirety. In preferred methods and compositions, the permeabilizers are one or more of cyclopentadecanone, cyclopentadecanolide, ethylene brassylate, or civetone. The permeabilizer may be administered prior to, concurrently with, or subsequent to delivery of the therapeutic agent to the tissue.

Methods according to the present invention may further include inducing hyperthermia in the tissue of interest. Preferably, inducing hyperthermia comprises elevating the temperature of the tissue and maintaining an elevated temperature for a period of time prior to, during, and/or following delivery of the agent to the tissue. Alternatively, acute hyperthermia may be employed.

In one aspect, the invention provides a method of enhancing the diffusion of a gene therapy vector through mammalian tissue. A preferred method according to this aspect of the invention comprises inducing hyperthermia in the tissue, delivering a permeabilizer to the tissue, and delivering the gene therapy vector to the tissue. Preferably, the permeabilizer and vector are delivered together.

The permeabilizer and hyperthermia act to increase the intercellular space of the tissue. At certain concentrations and temperatures, the process that increases the intercellular space is sufficient to effectively destroy the tissue. Thus, the present invention also provides a method of selectively destroying tissue. A preferred method according to this aspect of the invention comprises delivering a particular concentration of a permeabilizer to the tissue while inducing hyperthermia in the tissue and then maintaining hyperthermia.

In a further embodiment, the present invention provides a composition useful for performing in vivo, in vitro, or in situ gene therapy procedures in a tissue of interest. A preferred composition according to this aspect of the invention comprises an effective amount of the gene therapy vector that includes polynucleotide and an effective amount of a permeabilizer. The composition can be used with the methods of the present invention for performing gene therapy procedures.

DETAILED DESCRIPTION OF THE INVENTION

The present invention provides methods and compositions for enhancing the diffusion of a therapeutic agent through tissue. In one aspect, the invention provides methods and compositions for enhancing diffusion of a gene therapy vector through a mammalian tissue of interest during a gene therapy procedure. A preferred method according to this aspect of the invention involves delivering a permeabilizer to the tissue of interest and delivering a gene therapy vector to the tissue. The method may also include inducing hyperthermia in the tissue.

While preferred methods of the present invention are directed at gene therapy procedures, the present invention is not limited to these procedures. Indeed, the present invention is not limited to the use of gene therapy vectors as the therapeutic agent. The therapeutic agent can be any composition administered to a tissue. For example, the therapeutic agent can be a drug, protein, carbohydrate, or biomolecule, such as DNA or RNA. Essentially any composition that needs to enter and/or travel through a tissue following administration can comprise the therapeutic agent.

As indicated above, the therapeutic agent comprises a gene therapy vector in preferred methods and compositions. Essentially any agent that includes a polynucleotide can comprise a gene therapy vector. Preferably, the polynucleotide comprises a gene that encodes a protein, and preferably the protein is either capable of initiating death of the host cell or vector (e.g., a suicide gene and protein), or is a therapeutic protein (e.g. a replacement gene and protein for a genetic defect). Examples of known gene therapy vectors include polymeric molecules, genetic cassettes, phages, viruses and pseudo viruses. Viruses are currently the most frequently used vectors, and several types of viruses can be used as the gene therapy vector in the methods and compositions of the present invention. Examples of suitable virus vectors include papoviruses, lentiviruses, adenoviruses, vaccinia viruses, adeno-associated viruses, herpesviruses, and retroviruses.

During a gene therapy procedure, a polynucleotide is delivered to a tissue of interest by the gene therapy vector. The polynucleotide can be DNA, RNA, or any genetic construct made from nucleic acids. Preferably, the polynucleotide defines a cDNA or a gene or genes, i.e., a transgene or transgenes, that will be introduced into the cells of the tissue in an effort to either kill the host cell or vector (a suicide gene) or ameliorate a genetic defect (a therapeutic gene), such as a mutation or omission of a gene or genes. Examples of suitable suicide genes include thymidine kinase from Herpes simplex virus or cytosine deaminase from *Escherichia coli* or human microsomal p450 oxidoreductase. Examples of suitable therapeutic genes include the gene encoding insulin, the genes encoding cytokines such as interferon alpha, interferon gamma, interleukins, and the genes encoding membrane receptors such as receptors recognized by pathogenic organisms (viruses, bacteria or parasites), including the human immunodeficiency virus (HIV). This list of examples of suicide and therapeutic genes is merely exemplary in nature, and is not intended in any way to limit the scope of the present invention. The methods and compositions of the present invention can be utilized in any gene therapy procedure, and are not limited by the nature, type, or purpose of the polynucleotide utilized in the procedure.

Alternatively, the polynucleotide may not define a functional gene at all. Rather, the polynucleotide may simply define a length of nucleic acid to be introduced into the cell. For example, a small non-protein encoding sequence may be introduced into a cell to correct single or several point mutations.

Various gene therapy vectors containing appropriate genetic material for specific human maladies have been prepared and are known in the art. Frequently, vectors are designed to carry genes that trigger death of the host cell (i.e., suicide genes), therapeutic genes (i.e., genes that encode a therapeutic protein of some sort), or both. For example, U.S. Pat. No. 6,066,624 to Woo and Chen discloses adenovirus vectors having suicide and cytokine genes useful in gene therapy procedures for solid tumors. Also, U.S. Pat. No. 6,093,567 to Gregory et al. discloses an adenoviral vector for gene therapy procedures directed at cystic fibrosis. Other examples include retroviral gene therapy vectors (U.S. Pat. No. 6,140,111 to Riviere et al.) and herpesvirus gene therapy vectors (U.S. Pat. No. 6,106,826 to Brandt et al.).

Gene therapy procedures can be directed at a variety of mammalian tissues. In fact, essentially any tissue that can be accessed and infected by the vector can be the target of a gene therapy procedure. Also, gene therapy can be directed at a collection of cells that fall short of comprising tissue. Furthermore, other therapeutic agents, such as drugs, can be delivered to a great variety of mammalian tissues. Accordingly, the methods and compositions of the present invention can be utilized in conjunction with essentially any mammalian tissue. Examples of suitable tissue include, but are not limited to, muscle, neural, ocular, colon, prostate, breast, lung, skin, liver, bone, pancreas, ovary, testis, bladder, kidney, and brain tissue. The tissue can comprise essentially any tissue to which a therapeutic agent can be delivered by either systemic or local delivery methods. Preferably, the tissue comprises a solid tumor. That is, it is preferred that the tissue comprises a solid mass of cancerous cells. Particularly preferably, the solid tumor is a tumor derived from or located in muscle, neural, ocular, colon, prostate, breast, lung, skin, liver, bone, pancreas, ovary, testis, bladder, kidney, or brain tissue.

The permeabilizers for use in the methods and compositions of the present invention are one or more members from a family of macrocyclic compounds. As indicated above, this family of compounds is described in detail in U.S. Pat. No. 5,023,252. Briefly, the family has the general structure:

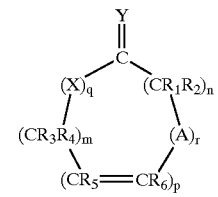

wherein X and Y are oxygen, sulfur or an imino group of the structure

or =N—R with the proviso that when Y is the imino group, X is an imino group, and when Y is sulfur, X is sulfur or an imino group, A is a group having the structure

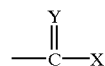

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are O, then m+n is at least 11. When R, $R_1$, $R_2$, $R_3$, $R_4$, $R_5$ or $R_6$ is alkyl, it may be methyl, ethyl, propyl, isopropyl, butyl, isobutyl, sec—butyl, amyl, hexyl, and the like.

This entire family of chemical compositions is collectively referred to herein as permeabilizers. Preferably, the permeabilizer comprises cyclopentadecanone, cyclopentadecanolide, ethylene brassylate, or civetone. This family and these permeabilizers offer several benefits and advantages, including being relatively non-toxic at low concentrations.

As discussed herein, all references to concentration values of the permeabilizer refer to the amount of permeabilizer present in the entire composition being discussed, such as a stock solution, working solution, or pharmaceutical composition. As appropriate for each permeabilizer, either weight or volume references are utilized.

Cyclopentadecanone and cyclopentadecanolide are solid, macrocyclic ketones. Consequently, these permeabilizers are preferably prepared as a liquid emulsion prior to delivery to the tissue of interest. That is, for cycolpentadecanone and cyclopentadecanolide, it is preferred that the solid compound be incorporated in a liquid to create a liquid emulsion. To facilitate preparation of these liquid emulsions, a stock emulsion of the permeabilizer can be prepared. Preferably, the stock emulsion contains a concentration of the permeabilizer that is higher than the concentration needed for the procedure. For example, stock emulsions containing 1–10% cyclopentadecanone or 1–25% cyclopentadecanolide (weight/volume) can easily be used to prepare working solutions having appropriate concentrations of the permeabilizer. A preferred stock emulsion comprises 6 percent (weight/volume) of the solid permeabilizer, e.g., cyclopentadecanone or cyclopentadecanolide, in a solution of 1.8% polysorbate 80 (volume/volume), 1.8% sorbitan monooleate (volume/volume), and glycerol phosphate buffered Saline (PBS). Following preparation, this mixture is autoclaved at 121° Celsius for 20 minutes and then periodically agitated as it cools in a 70°–80° Celsius water bath. Once the emulsion has reached 70° Celsius, it is removed to room temperature where it is stable for several months. If some phase separation occurs, the emulsion is re-established by heating the mixture at 50°–70° Celsius for 20 minutes, with periodic agitation. More or less concentrated stock emulsion can be made by adjusting the permeabilizer and other emulsion components percentages proportionately. The permeabilizer stock solutions can be diluted to lower concentration working solutions using an emulsion of 1.8% polysorbate 80 (volume/volume) and 1.8% sorbitan monooleate glycerol (volume/volume) in PBS.

Ethylene brassylate and civetone are both liquids and can therefore be delivered to a tissue of interest without any further manipulation. Preferably, however, these permeabilizers are also prepared as liquid emulsions prior to administration to a tissue. Furthermore, stock emulsions of these permeabilizers can also be prepared. Both of these permeabilizers can be added to the other emulsion components, as described above for cyclopentadecanone and cyclopentadecanolide, at a volume to volume ratio. The remainder of the emulsion preparation is preferably as described above for cyclopentadecanone and cyclopentadecanolide.

As indicated above, prior to delivery to the tissue of interest, a working emulsion of the permeabilizer is prepared, preferably from one of the stocks. The working emulsion preferably comprises one or more permeabilizers in a buffer. The concentration of the permeabilizer will depend on the permeabilizer used in the procedure being conducted. Because ethylene brassylate and civetone are liquids, they can be administered to a tissue at concentrations up to 100%. Preferably, the working emulsion contains ethylene brassylate, civetone, or a combination of both at a concentration of between approximately 0.1 and 20% (volume/volume). As indicated above, Cyclopentadecanone and cyclopentadecanolide, however, are solids. The highest concentration of cyclopentadecanone or cyclopentadecanolide that can be made into a stable emulsion is approximately 25% (weight/volume). As a result, the working emulsion preferably contains cyclopentadecanone or cyclopentadecanolide at a concentration of between approximately 0.1 and 25%. Particularly preferred is a working solution that contains cyclopentadecanone, cyclopentadecanolide, or a combination of both, at a concentration of between approximately 0.1 and 7%.

No matter the permeabilizer chosen, the concentration used will depend on several factors and should be optimized accordingly. Factors that affect the preferred concentration include the size of the tissue, the extent of diffusion desired, the fibrosity of the tissue, and the location of the delivery site relative to the center and/or perimeter of the tissue. For example, when solid tumors comprise the tissue of interest, higher concentrations of permeabilizer facilitate diffusion even through tumors that are relatively fibrous, i.e. dense, in nature.

The buffer is preferably a solution that confers upon the working solution a pH that is suitable for the tissue of interest. For example, it is preferable that the working solution has a pH of between approximately 6 and 8. Particularly preferred is a buffer that confers a pH of approximately 7.4. Also, the buffer preferably confers upon the working solution a salinity level, i.e., salt concentration, that is suitable for the tissue of interest. For example, when human tissue comprises the tissue of interest, it is preferred that the working solution have a salinity level of approximately 0.9%.

In addition using a single permeabilizer, any combination of permeabilizers can be used in methods and compositions according to the present invention. In fact, mixing permeabilizers increases the amount of the solid permeabilizers that can be included in a stock emulsion.

The permeabilizer can be delivered to the tissue of interest in any of a variety of manners. For example, systemic delivery routes such as intravenous injection can be utilized. Preferably, however, the permeabilizer is directly delivered to the tissue of interest. This direct delivery is preferably accomplished by a direct injection technique. Direct injection can be accomplished using a syringe, needle, or other delivery device suitable for delivering therapeutic agents to tissue. When the tissue of interest comprises a solid tumor, the permeabilizer can be injected with a standard syringe into the tissue mass. Preferably, using this technique, the syringe is inserted into the tissue at a depth and position that ensures delivery of the permeabilizer to the approximate geometric center of the tissue mass. Alternatively, the position at which the permeabilizer is delivered can be varied according to the needs behind the procedure being conducted.

The permeabilizer can be delivered to the tissue of interest prior to, concurrently with, or subsequent to the delivery of the therapeutic agent to the tissue. In a preferred embodiment, in which the therapeutic agent comprises a gene therapy vector, it is preferred that the permeabilizer be delivered to the tissue either prior to or concurrently with delivery of the gene therapy vector. Particularly preferred is a method in which the gene therapy vector is delivered to the tissue along with the permeabilizer, i.e., as part of the same composition. Accordingly, a preferred composition in accordance with the present invention includes both the gene therapy vector and the permeabilizer, as will be developed more fully below.

The methods of the present invention may also include inducing hyperthermia in the tissue of interest. That is, the methods of the present invention can include elevating the temperature of the tissue of interest to a temperature above the normal body temperature for the host. For example, in procedures involving humans, the temperature of the tissue is elevated to a temperature above normal human body temperature, 37° C. The temperatures and ranges discussed herein are for human hosts, but it will be readily recognized that appropriate hyperthermia can be induced in other animals by determining the normal body temperature of the animal and elevating the temperature of the tissue to a comparable temperature above the normal body temperature.

The inventor has discovered that hyperthermia has several beneficial effects on the methods of the present invention. For example, hyperthermia enhances the effect of the permeabilizers, providing for a greater increase in interstitial space and, ultimately, an increased breakdown of membranes. Also, hyperthermia allows for a lower effective dose of the permeabilizer and vector. Furthermore, hyperthermia allows for a two-pronged approach to tumor therapy. For example, a method according to the present invention can include inducing hyperthermia in a tumor to destroy the center or core of the tumor, and delivering vectors to the tumor to treat or kill cells on the periphery or margin of the tumor.

While an elevated temperature increases the ability of the permeabilizer to enhance diffusion of the therapeutic agent through the tissue of interest, it may not be desirable to increase the temperature of other tissues of the animal undergoing treatment with the therapeutic agent. Therefore, the hyperthermia is preferably localized to the tissue of interest. Devices and methods of accomplishing localized hyperthermia are known (see, for example, U.S. Pat. No. 6,176,857 to Ashley) and can be used to accomplish the desired effect. Alternatively, hyperthermia can be induced in the general anatomical area that contains the tissue of interest. Also alternatively, the temperature of the animal undergoing the treatment with the therapeutic agent can be raised a suitable level.

The effects of the hyperthermia are greatest when the elevated temperature is maintained in the tissue for a duration of time. Therefore, it is preferred that the elevated temperature be maintained in the tissue of interest for a set period of time.

The increase in the temperature of the tissue of interest will depend upon several factors, including the type of procedure being conducted. Preferably, the temperature of the tissue of interest is elevated to between approximately 38° and 45° C. For procedures in which it is desirable to enhance the diffusion of the therapeutic agent through the tissue of interest, it is preferred that the temperature of the tissue is elevated to approximately 41° C. For procedures in which it is desirable to destroy the tissue of interest, it is preferred that the temperature of the tissue is elevated to approximately 43–45° C.

The length of time during which the temperature of the tissue of interest remains elevated will also depend upon several factors. Preferably, for procedures in which is desirable to enhance the diffusion of the therapeutic agent through the tissue of interest, the elevated temperature is maintained until the agent diffuses through the tissue of interest. That is, it is preferable that the elevated temperature be maintained in the tissue of interest until the therapeutic agent diffuses throughout the tissue of interest. Appropriate times can be determined for specific permeabilizer and tissue combinations. The time can be determined for the therapeutic agent being utilized as appropriate by standard methods. Preferably, the elevated temperature is maintained in the tissue of interest for between approximately one hour and up to 72 hours. The duration of maintaining the elevated temperature may be brief, extended, or even intermittent in nature. Similar to the concentration of the permeabilizer, the preferred duration of hyperthermia will depend on several factors, and should be optimized accordingly. Appropriate end points for hyperthermia include completion of diffusion through the tissue (for enhancement).

For procedures in which a permeabilizer is being used to destroy a tissue of interest, it is preferable that an elevated temperature be maintained for an extended period of time. Preferably, the elevated temperature is maintained in the tissue of interest until the morphology of the tissue changes into a gelatinous mass. That is, it is preferred that the elevated temperature be maintained in the tissue until damage occurs to the integrity of the cell. For example, it is preferred that, for destruction of tissue, hyperthermia be maintained until the cell membranes of the individual cells comprising the tissue begin to degrade and the separation between cells becomes less well-defined.

Inducing hyperthermia in accordance with the methods of the present invention can be accomplished in a variety of manners. Essentially any technique that produces an appropriate increase in temperature in the tissue of interest can be used. Preferably, techniques of raising temperature in tissue that allow for maintaining the elevated temperature over a period of time are used.

Several methods of inducing hyperthermia in tissue have been described. U.S. Pat. No. 6,167,313 to Gray, et al., provides an overview of several techniques and methods. Any standard technique can be used to accomplish the desired hyperthermia. For example, an ultrasonic transducer can be employed to deliver a localized increase in tissue temperature. For an example of methods and apparatuses in accordance with this category, see U.S. Pat. No. 5,620,479 to Diederich. Alternatively, a technique commonly referred to as interstitial hyperthermia can be employed. Other alternative methods of inducing hyperthermia include exposing the tissue to microwave radiation (for example, see U.S. Pat. No. 5,861,021 to Thome et al. and U.S. Pat. No. 5,922,013 to Fallick) or magnetic induction (see the '313 patent).

The method employed to induce hyperthermia can be optimized based upon the nature of the tissue of interest. For example, for deep tissues, such as a tumor in prostate tissue, interstitial hyperthermia will likely offer a better ability to control the hyperthermia. For surface tissues, a simple device, such as an ultrasonic transducer, will likely by sufficient.

Hyperthermia can be induced prior to, contemporaneously with, and/or subsequently to delivery of permeabilizer to the tissue of interest. Furthermore, hyperthermia can be induced prior to, during or following the delivery of the therapeutic agent to the tissue. When it is desired to induce hyperthermia prior to delivery of permeabilizer to the tissue of interest, the tissue is preheated to the prescribed hyperthermic temperature and then the permeabilizer is delivered to the tissue. It is preferred that hyperthermia is continued during the delivery process.

Compositions according to the present invention comprise pharmaceutical compositions that include an effective amount of a therapeutic agent and an effective amount of a permeabilizer. Further, the composition may include a buffer. As used herein, the term effective amount of a therapeutic agent refers to an amount of the agent that is sufficient to achieve the objective of the therapy. Regarding gene therapy vectors, an effective amount refers to a quantity of vectors that is sufficient to confer a certain likelihood of the vector being introduced into the cells and the incorporation and/or expression of the polynucleotide into the cell. An effective amount of a permeabilizer refers to the various concentrations of permeabilizers discussed in detail above.

In a preferred composition, an effective amount of a gene therapy vector and an effective amount of a permeabilizer are added to a buffer solution. The buffer can be essentially any buffer that can be administered to the tissue of interest. Preferably, the buffer does not increase the toxicity characteristics of the vector and permeabilizer, and is suitable to maintain the pH of the composition of between approximately 6 and 8. A solution of 1.8% polysorbate 80 (volume/volume) and 1.8% sorbitan monocleate (volume/volume) glycerol in PBS is a suitable buffer. As indicated above, the buffer more preferably confers a pH of about 7.4 and a salinity of about 0.9% onto the composition.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. As such, the Examples are not to be construed to limit the invention to these preferred modes. Furthermore, those of skill in the art should, in light of the present disclosure, appreciate that many changes can be made in the specific embodiments that are disclosed and still obtain like or similar results without departing from the spirit and scope of the invention.

Example 1

Spheroids of MCF-7 Human Breast Carcinoma Cells Treated with Doxorubicin and Cyclopentadecanone Spheroids made from MCF-7 human breast carcinoma cells were treated with 3.0 micrograms per milliliter doxorubicin for six hours at various temperatures and under various permeabilizer conditions. Doxorubicin is an antineoplastic drug frequently used in chemotherapy procedures. When the spheroids were treated for six hours at 37.0° C. in the absence of permeabilizer, the drug penetrated only six cell layers into the spheroids. In contrast, when doxorubicin was administered in culture medium containing 0.6% cyclopentadecanone at 37.0° C., the degree to which the drug penetrated the spheroids essentially tripled. The spheroids in this experiment also underwent a characteristic change in morphology. The whole, unsectioned spheroids exhibited a rougher, more uneven perimeter along which individual cells could be discerned. Spheroid sections showed the rougher perimeter was due to an increase in intercellular space, which was more pronounced at the spheroid perimeter, but was still discernible deeper inward. These changes in spheroid morphology and drug penetration were never observed in control spheroids that received no permeabilizer treatment. Furthermore, these changes were never observed in spheroids that received sham treatment, which included exposure to all components used in the permeabilizer emulsion except the permeabilizer.

Example 2

Spheroids of MCF-7 Human Breast Carcinoma Cells Treated with Doxorubicin, Cyclopentadecanone and Hyperthermia In this example, spheroids were treated as in example 1 with the addition of hyperthermia as an additional variable in the experiment. Hyperthermia in this example involved raising the temperature of the spheroids to approximately 40° C. When hyperthermia was administered concurrently with delivery of the permeabilizer, a marked potentiation of permeabilizer activity resulted. A greater increase in intercellular space was observed in both intact and sectioned spheroids. Also, the doxorubicin penetrated all recesses of the spheroids such that every cell within the spheroids exhibited strong doxorubicin fluorescence upon detection of the presence of the drug. Hyperthermia treatment alone had no effect on penetration of doxorubicin or upon the intercellular space.

Example 3

Spheroids of Du-145 Human Prostate Carcinoma Cells Treated with Adenovirus Vectors, Cyclopentadecanolide and Hyperthermia The increase in intercellular space produced by cyclopentadecanolide in the previous examples was large enough to be discernible with low magnification light microscopy. This Example comprised experiments to demonstrate that the increase in the intercellular space was sufficient to permit increased penetration of adenovirus gene therapy vectors into the spheroids treated with permeabilizer alone, or permeabilizer in conjunction with hyperthermia. The spheroids made from DU-145 human prostate carcinoma cells were grown to an average diameter of 500 micrometers and then suspended in culture medium containing 0.1% to 3% cyclopentadecanolide plus adenovirus vectors that had beta-galactosidase as a reporter transgene. Once a viral vector entered a cell, beta-galactosidase was expressed constitutively under control of the human CMV promoter. The experimental protocol called for the spheroids to be incubated for 48 to 72 hours following treatment to permit transgene expression. It should be noted that a reporter gene was utilized in this Example, as well as in Examples 4 and 5, only to facilitate determination of the extent of vector diffusion. Any other polynucleotide could be used in this system, including suicide genes and genes encoding therapeutic proteins.

Within 6 to 24 hours following permeabilizer treatment, depending upon the permeabilizer concentration used, the cells within the spheroid regions where the intercellular space was increased became detached from the spheroid. This effect was grossly exacerbated when hyperthermia was included in the treatment. The cells that detached from the spheroids were collected and were shown later to exhibit beta-galactosidase activity.

Example 4

Du-145 Xenograft Tumors Treated with Adenovirus Vectors and Cyclopentadecanolide Du-145 tumors grafted onto mice were injected with cyclopentadecanolide and adenovirus vector that contained the beta-galactosidase transgene, all in PBS. The tumor was retrieved 72 hours after treatment, cryosectioned, and stained with X-gal to visualize beta-galactosidase expression. In tumors that received a single injection of 30 microliters containing 12% cyclopentadecanolide and $2 \times 10^{10}$ adenovirus vectors, the reactive staining from beta-galactosidase expression was pervasive throughout the section.

Example 5

Du-145 Xenograft Tumors Treated with Adenovirus Vectors, Cyclopentadecanolide and Hyperthermia In this example, tumors were heated to 41.0° C. using an unfocused ultrasonic transducer prior to treatment with permeabilizer and virus vector. When hyperthermia was established, the tumor was given a single injection of 30 microliters containing 6% cyclopertadecanolide and $2\times10^{10}$ adenovirus vectors that contained the beta-galactosidase transgene, all in PBS. Following the injection, the hyperthermia was continued for an additional 45 minutes. That is, the elevated temperature was maintained for 45 minutes after injection. The tumor was retrieved 72 hours following the injection, cryosectioned, and stained with X-gal to visualize beta-galactosidase expression.

Tumor sections from this example revealed large voids in the center of the sections. The voids were filled with light amber colored, gelatinous material, indicating break-down of the tissue cell membranes. Although staining indicative of beta-galactosidase expression pervaded the remainder of the sections, many vacuoles and voids were also present in these areas.

The references cited in this disclosure, except to the extent they may contradict any statements or definitions made herein, are each hereby incorporated by reference in their entirety.

The foregoing disclosure is the best mode devised by the inventor for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations, and should be limited only by the spirit and scope of the following claims:

What is claimed is:

1. A method of enhancing diffusion of a therapeutic agent through a mammalian tissue, comprising:

delivering said therapeutic agent to said tissue;

delivering a permeabilizer to the tissue; and using a device to elevate the temperature of the tissue to above normal body temperature; wherein the permeabilizer is of the structure:

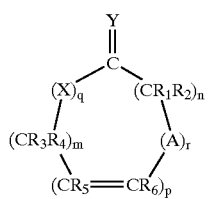

wherein X and Y are oxygen, sulfur or an imino group of the structure

or =N—R with the proviso that when Y is the imino group, X is an imino group, and when Y is sulfur, X is sulfur or an imino group, A is a group having the structure

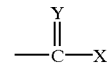

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are O, then m+n is at least 11.

2. The method according to claim 1, wherein elevating the temperature of the tissue comprises elevating the temperature of the tissue to between approximately 37.5 and 43° C.

3. The method according to claim 2, further comprising maintaining the elevated temperature for approximately 1 to 72 hours.

4. The method according to claim 2, wherein the temperature is approximately 41° C.

5. The method according to claim 1, wherein elevating the temperature of the tissue is accomplished by delivering ultrasonic energy to the tissue, delivering microwave energy to the tissue, or by delivering magnetic energy to the tissue.

6. The method according to claim 1, wherein elevating the temperature of the tissue occurs prior to delivering permeabilizer to the tissue.

7. The method according to claim 1, wherein elevating the temperature of the tissue occurs subsequently to delivering permeabilizer to the tissue.

8. The method according to claim 1, wherein the permeabilizer comprises two or more permeabilizers.

9. The method according to claim 1, wherein the permeabilizer is a member selected from the group consisting of cyclopentadecanone and cyclopentadecanolide.

10. The method according to claim 9, wherein the permeabilizer is cyclopentadecanone.

11. The method according to claim 9 wherein the permeabilizer is delivered in a pharmaceutical composition comprising the permeabilizer and a buffer.

12. The method according to claim 11, wherein the permeabilizer is from about 0.1 to 25% by weight of the pharmaceutical composition.

13. The method according to claim 1, wherein the permeabilizer is a member selected from the group consisting of ethylene brassylate and civetone.

14. The method according to claim 13 wherein the permeabilizer is delivered in a pharmaceutical composition comprising the permeabilizer and a buffer.

15. The method according to claim 13, wherein the permeabilizer is from about 0.1 to 100% by volume of the pharmaceutical composition.

16. The method according to claim 1, wherein said therapeutic agent is a vector containing a polynucleotide.

17. The method according to claim 16, wherein the polynucleotide comprises a suicide gene.

18. The method according to claim 16, wherein the polynucleotide comprises a gene encoding a therapeutic protein.

19. The method according to claim 14, wherein the gene therapy vector comprises a member selected from the group consisting of parvovirus, lentivirus, adenovirus, vaccinia virus, adeno-associated virus, herpesvirus, and retroviruses.

20. The method according to claim 1, wherein delivering the permeabilizer comprises directly infusing the permeabilizer into the tissue.

21. The method according to claim 1, wherein the tissue comprises a solid tumor.

22. The method according to claim 21, wherein the solid tumor is a member selected from the group consisting of colon, prostate, breast, lung, skin, liver, bone, pancreas, ovary, testis, bladder, kidney, brain, and head and neck tumors.

* * * * *

UNITED STATES PATENT AND TRADEMARK OFFICE
CERTIFICATE OF CORRECTION

PATENT NO.   : 6,794,376 B2                              Page 1 of 1
DATED        : September 21, 2004
INVENTOR(S)  : Michael J. Borrelli It is certified that error appears in the above-identified patent and that said Letters Patent is hereby corrected as shown below:

<u>Column 12,</u>
Lines 1-4, change "$\substack{Y \\ \| \\ -C-X}$" to -- $\substack{Y \\ \| \\ =C-X}$ --.

Line 10, after "$R_1$" delete "$R_1$"

Signed and Sealed this

Twelfth Day of April, 2005

JON W. DUDAS
*Director of the United States Patent and Trademark Office*